United States Patent [19]
Park et al.

[11] Patent Number: 6,004,323
[45] Date of Patent: Dec. 21, 1999

[54] SURGICALLY IMPLANTABLE FASTENING SYSTEM

[75] Inventors: Joon B. Park, Coralville; Vijay K. Goel, Iowa City; Malcolm H. Pope, Coralville; James N. Weinstein, Iowa City, all of Iowa

[73] Assignee: The University of Iowa Research Foundation, Iowa City, Iowa

[21] Appl. No.: 08/795,611

[22] Filed: Feb. 4, 1997

[51] Int. Cl.$^6$ .................................................. A61B 17/58
[52] U.S. Cl. .................................................. 606/61; 606/77
[58] Field of Search ....................... 606/77, 76, 73, 606/61, 70, 71, 69, 86, 105

[56] References Cited

U.S. PATENT DOCUMENTS

| | | |
|---|---|---|
| 3,552,389 | 1/1971 | Allgower et al. . |
| 3,596,656 | 8/1971 | Kaute . |
| 3,779,240 | 12/1973 | Kondo . |
| 4,338,926 | 7/1982 | Kummer et al. ........................ 606/70 |
| 4,388,921 | 6/1983 | Sutter et al. . |
| 4,513,744 | 4/1985 | Klaue . |
| 4,611,581 | 9/1986 | Steffee . |
| 4,787,657 | 11/1988 | Henniger ............................... 285/323 |
| 4,836,196 | 6/1989 | Park et al. . |
| 4,907,924 | 3/1990 | Hellon ..................................... 411/303 |
| 4,943,292 | 7/1990 | Foux . |
| 5,013,315 | 5/1991 | Barrows .................................. 606/71 |
| 5,057,111 | 10/1991 | Park . |
| 5,084,051 | 1/1992 | Tormala et al. ......................... 606/77 |
| 5,108,399 | 4/1992 | Eitenmuller et al. ................... 606/77 |
| 5,234,431 | 8/1993 | Keller . |
| 5,337,641 | 8/1994 | Duginske ................................ 83/468 |
| 5,357,414 | 10/1994 | Dane et al. ............................. 362/431 |
| 5,388,941 | 2/1995 | Wuenscher ............................. 411/369 |
| 5,390,683 | 2/1995 | Pishardi ................................. 606/61 |

FOREIGN PATENT DOCUMENTS

WO 94/16634  8/1994  WIPO .

OTHER PUBLICATIONS

Park and Lakes, Editors, "Biomaterials: An Introduction," pp. 150–151, Plenum Press, New York and London, 1992.

*Primary Examiner*—Michael Buiz
*Assistant Examiner*—Vy Quang Bui
*Attorney, Agent, or Firm*—Arnold White & Durkee

[57] ABSTRACT

The present invention discloses a nut to be used in a spinal screw and plate assembly to affix the screw and plate assembly to the spinal bone. The nut has a polymer insert that when contacted with a screw allows a bone plate and screw structure to relax over time.

25 Claims, 7 Drawing Sheets

CONTROL

POLYMER INSERT

SURGICALLY IMPLANTABLE FASTENING SYSTEM

BACKGROUND OF THE INVENTION

A. Field of the Invention

The present invention relates generally to the field of healing bone fractures. More particularly, it concerns apparatus and methods for healing bone fractures by controlling the load transmitted to the fractures throughout the healing process.

B. Description of the Related Art

Spinal columns are prone to deformation and degeneration. These conditions often require corrective surgery. In some surgical procedures it is necessary to remove the intervertebral discs from the damaged part of the spinal column. Bone grafts may then be placed in the position vacated by the disc and the bone graft and vertebrae to be fused are held in a desired position for healing using a device connected to vertebrae on either side of the bone graft. Such a device maintain the vertebrae in a desired position for healing and further prevents the transmission of load through the bone graft while the graft is healing. Devices for the connection of vertebral bodies are disclosed in U.S. Pat. Nos. 4,611,581 and 4836196.

In other procedures the healing of fractured long bones employs implantable plates for internal fixation. The concept is to place a plate in contact with the fractured bone such that the plate spans the fracture, and to fasten the plate to the bone on both sides of the fracture. Compression plates typically are attached to the bone by screws and nuts that act to transfer the load from the bone to the plate and force the broken ends of the bone together. Typical fracture fixation compression devices are disclosed in U.S. Pat. Nos. 4,943,292, 4,513,744, 3,779,240, and 3,552,389.

In a typical situation, use of a conventional bone fracture compression plate made of high modulus 316L stainless steel (200 GPa; $30 \times 10^6$ psi), may result in stress-shielding the bone under the plate causing a weakening of the cortical bone (at about 15 GPa) under the plate. Relieving the bone from carrying a load over an extended period of time may thus contribute to the development of this type of bone weakening or osteoporosis, also known as osteopenia. When the plate and screws are removed from the healed bone, a re-fracture may result due to such weakening.

Attempts to solve this problem have included the fabrication of the fracture plates from materials that are less rigid than 316L stainless steel. For example, titanium alloys, composites, and resorbable materials have been utilized. Each of these materials, however, presents additional problems.

Bioresorbable bone plates have been investigated by Christal et al.,(1984). A major problem associated with resorbable bone plates made of polyglycolic acid (PGA) or polylactic acid (PLA) polymers is the release of polymer residues into the body. While it is unclear whether these polymer residues produce any side effects, the precise control of the dissolution rate of these polymers over the entire plate is difficult, if not impossible, to control. Moreover, the screws for securing the bone plate to the bone cannot be made from these materials because these materials lack the requisite torsional strength. Hence, conventional metal screws are used, and a secondary operation is needed to remove the screws even when the plates are made of resorbable materials.

One of these conventional compression plate assemblies (U.S. Pat. No. 5,057,111 to Park) utilizes a spacer placed between the screw and the nut to allow the plate to move slightly, resulting in the load being transmitted differentially between the compression plate assembly and the bone. As the bone fracture heals, a greater load is transmitted to the bone. The spacer is made of a material which plastically deforms as a function of time and load transmitted therethrough to decrease the load transmitted between the structure and the fastener. This movement of the fracture plate relative to the bone is known as creep.

The deposit of polymer residue near the site of the wound may be deleterious to the healing process if the spacer breaks down. Also. there is little control over the rate of creep due to changes in the polymer. Thus, here exists a need for a nut for use in securing a bone plate to a bone that allows creep while controlling the unwanted escape of polymer particles.

SUMMARY OF THE INVENTION

The present invention addresses these problems by encasing a polymer insert in a nut in such a way as to reduce the deposition of insert polymer into the surrounding environs while providing controllable creep.

The invention concerns a surgically implantable nut with polymer insert to be used in exemplary embodiments with the spinal pedicle plate, screw, and nut assembly for the fusion of spinal segments. A feature of this nut is the use of a plastic insert, such as an ultra high molecular weight polyethylene (UHMWPE) insert, which prevents the loosening of the nut by virtue of the extra friction generated between screw and polymer and polymer and the surface of the nut. An advantage of using UHMWPE is that it has previously been used as an implant material in such items as the acetabular cup of hip joints and tibial plateau of knee joints. In addition to UHMWPE, other suitable polymer inserts include, but are not limited to, polyethylene, polytetrafluoroethylene, polycarbonate, nylon, styrene butadiene rubber, VITON® copolymers, butyl rubber, or nitrile rubber which is biocomapatible and has physical features similar to UHMWPE.

The present invention includes a nut-like fastener for connecting a surgically implantable device to a fractured bone that comprises a nut casing defining an axial central passageway having an outside surface and an inside surface, and a relaxative polymeric material lining the inside surface of the nut. The polymeric lining or sleeve is adapted to engage a screw in a firm threaded relationship, and plastically deforms as a function of time and stress. In certain embodiments, the polymeric lining is bioresorbable. Where the polymeric lining is bioresorbahle, the material may be composed of polylactic acid. polyglycolic acid copolymers of PGA, collagen, and the like. The outer wall of the sleeve is sized to fit securely within the nut body or shell. The inner wall of the sleeve is sized, and may be threaded, to engage a screw fastener in a friction-held fit.

The casing or body of the nut is composed of a biocompatible material that is rigid and durable. Such material may be, for example, stainless steel, a cobalt-chromium-molybdenum alloy or a titanium alloy. The nut casing has a hexagonal, square, or the like shape to the shell to facilitate engagement with a tool used for tightening the nut. At least one end of the nut casing preferably includes a deformable lip around its inner periphery to be deformed around the end of the polymeric lining to maintain the polymeric insert within the nut body. The screw, however, is able to move through the deformed lip. In other embodiments, the nut may be formed so as to include a small shoulder at one end of its passageway to hold the plastic sleeve in place.

It is important that the polymeric material liner or sleeve in each nut body be held firmly within the device. The outer surface of the liner may be held by friction, cement or other suitable means to the shell of the device. The inner surface is sized to receive the threaded exposed end of a screw or other rod-like member as described earlier in a friction-tight threaded relation.

In some embodiments, the nut utilized in the fastening system is adjusted by selective tightening thereby adjusting the load transmitted between the bone and the pedicle plate. Also, the nut is tightened to allow creep over time. This may be accomplished by use of a suitable drive tool, which may comprise a screw driver, wrench, torque wrench, or other like device that is capable of applying a particular, known torque.

The invention may also comprise a fastener for securing a surgically implantable device that comprises a nut casing which is biocompatible and has a central passageway, and has a relaxative polymeric member insertable within the passageway and capable of engaging a screw member in a threaded relation. By the term "relaxative," it is meant that the polymeric member plastically deforms as a function of time and stress. This structural tendency to deform or creep under stress is one aspect of the relaxative nature of the polymer. In this embodiment, the polymeric member that plastically deforms may be, for example, polyethylene, polytetrafluoroethylene, polycarbonate, nylon, styrene butadiene rubber, VITON® copolymers, butyl rubber, or nitrile rubber.

The top surface of the nut may be a solid surface, or capped, to prevent polymeric material from escaping. In certain embodiments, the polymeric member comprises a threaded inside surface, and in other embodiments, the polymeric member has a smooth inside surface.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention, in a preferred embodiment, concerns a system for holding two or more spinal segments together after removal of discs while gradually releasing the compressive forces which the system applies to the portions. An important feature of the system lies in a fastener which controls the release of the compressive forces.

One such fastener is shown in FIG. 1A, FIG. 1B, FIG. 1C, and FIG. 1D in the form of a nut which comprises a rigid biocompatible casing 1 that houses a polymer insert 2. Lip 4 is bendable, and is designed to hold polymer insert 2 inside casing 1 upon insertion. A central passageway 3 in the polymer insert is for the threaded portion of a screw of any given size to be used in a surgical implantation. It is recognized that a nut of the present invention may be of different sizes, depending on the size of the screw. This, in turn, is dependent on the type and size of the spinal segments to be fused. The nut may be further defined as a relaxative fastener. The top of the nut may be open or sealed.

Figure 1A:
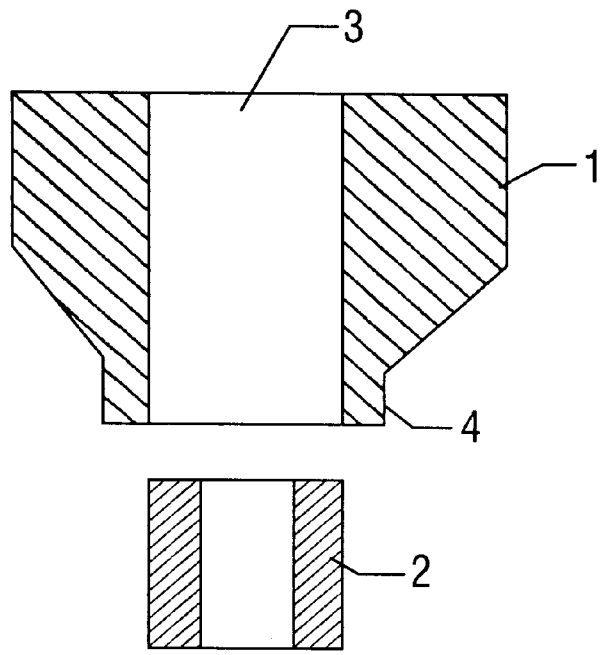
FIG. 1A shows a cut away view of a nut casing of the present invention.
Figure 1B:
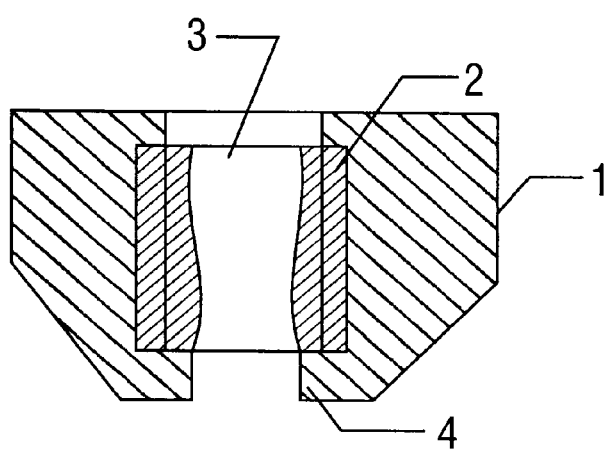
FIG. 1B shows the nut of the present invention with the polymer insert held in place inside the nut casing.
Figure 1C:
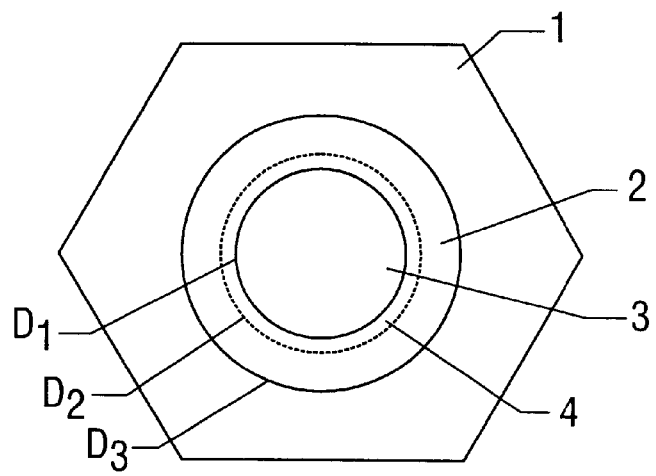
FIG. 1C shows a top surface view of the nut of FIG. 1A. 1 is the nut casing, 2 is the polymeric insert, 3 is the passageway for accommodation of screw therethrough, and 4 is the lip. $D_1$ is the diameter of the passageway, $D_2$ is the diameter of the lip and $D_3$ is the internal diameter of the nut casing.
Figure 1D:
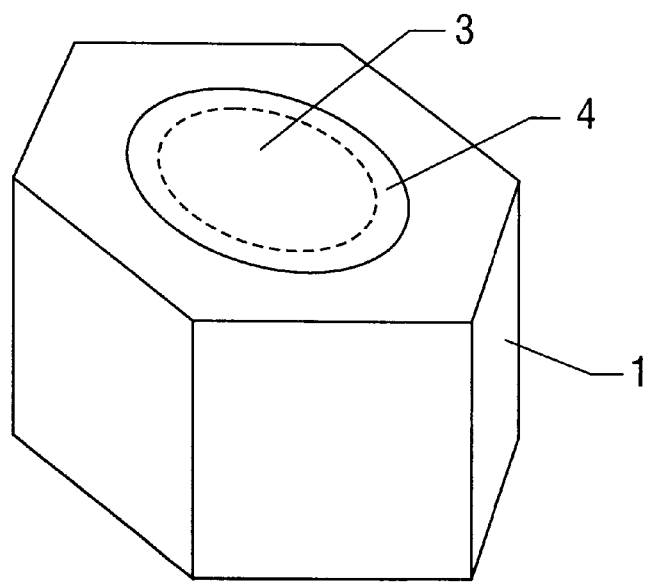
FIG. 1D shows a perspective view of the nut of FIGS 1A and 1B.

FIG. 1B is a side cutaway view of the assembled nut, and shows nut casing 1 with polymeric insert 2 held in place by lip 4. In this view, polymer insert was placed inside nut casing 1 and lip 4 was bent to hold polymer insert in place. Central passageway 3 is for accommodation of a screw or other fastening rod.

As embodied herein the implements for attaching the plate to the boney spinal tissue may comprise screws, nails, pins and the like, referred to herein as "bone fasteners". One end of the bone fastener is embedded into the spinal tissue, while the other end is configured with threads to allow a nut to be threaded in place.

Preferably, the bone fasteners are made of a sufficiently rigid and durable material that is biocompatible. Examples of metallic materials that fulfill the durability and rigidness requisites and are also biocompatible include stainless steel, cobalt-chromium-molybdenum alloys or titanium alloys commonly used in implantable medical devices. Of course these are only exemplary materials and persons skilled in the art will recognize that other materials are equally suitable.

Figure 2:
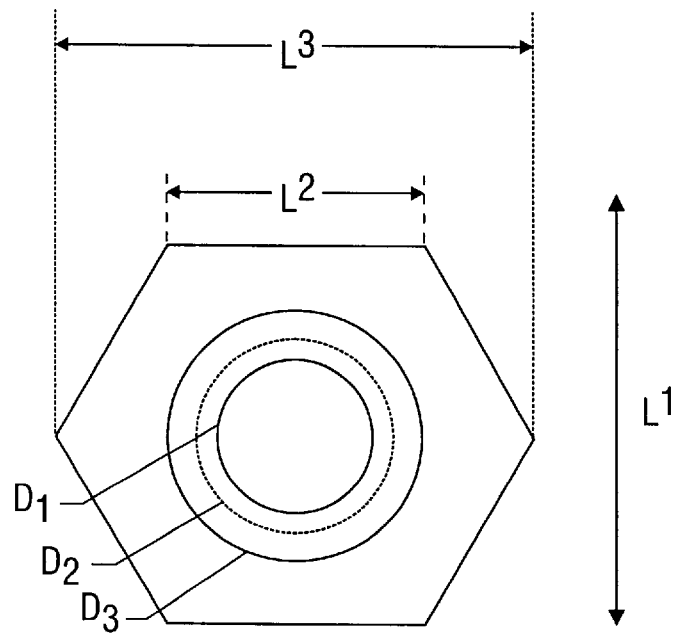
FIG. 2 shows a polymer containing nut of the invention with representative dimensions. where $D_1$ is about 0.165 inch, $D_2$ is about 0.185 inch, $D_3$ is about 0.25 inch, $L^1$ is about 0.433 inch, $L^2$ is about 0.25 inch and $L^3$ is about 0.5 inch.

An example of a nut fastener of the present invention that may be used to secure a plate to a long bone is shown in FIG. 2. In this figure, $D_1$ is the diameter of the hole in the nut and is about 0.16 inch. $D_2$ is the diameter of the lip of the nut and is about 0.18 inch, $D_3$ is the diameter of the polymer insert and is about 0.25 inch, $L_1$ is about 0.43 inch, $L_2$ is about 0.25 inch and $L_3$ is about 0.5 inch.

The nut has an internal diameter $D_3$ into which a cylindrical polymeric or plastic insert is placed. Once the insert is in place, lip 4 of diameter $D_2$ is bent over and a passage of the desired size of diameter $D_3$ for the screw is drilled. The polymer insert as used herein can form a lining on the inside of the nut. "Lining" means coating the inside surface of the nut casing with a material from 0.5 mm to 3 mm in width. Of course it is understood that these measurements may vary according to the size of the nut.

Figure 3:
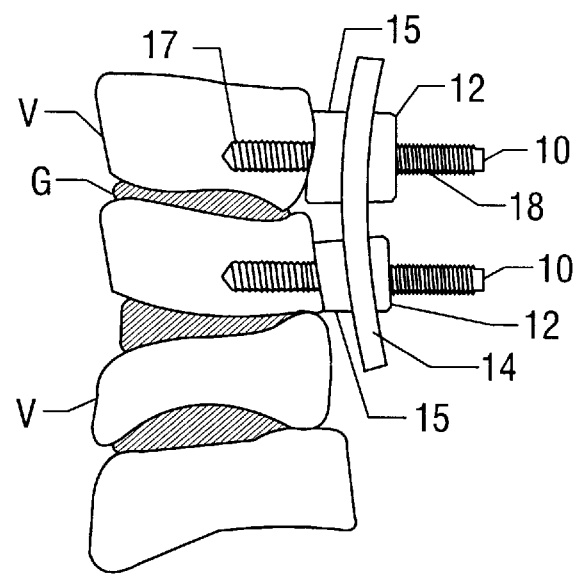
FIG. 3 shows a view in section of the discetomied spinal segments being held together by an apparatus embodying the present invention.
Figures 4A, 4B:
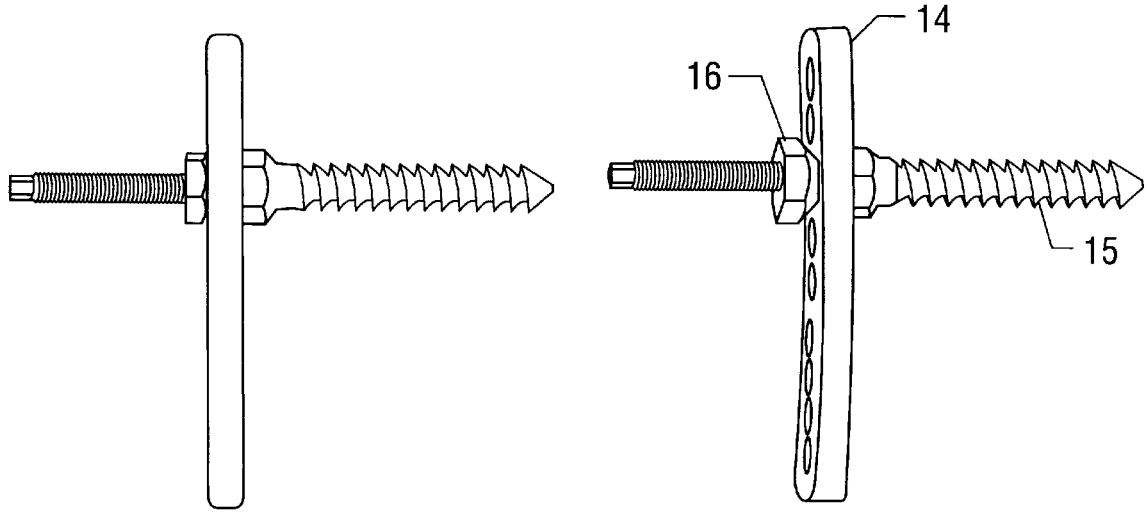
FIG. 4 is an assembled view of the pedicle plate and screw showing the control nut without the polymer insert and the polymer containing nut of the present invention.

An example of an apparatus in which the present invention may be used is shown in FIG. 3. A rigid plate 14, having a top or outer surface 6 and a bottom or inner surface 7. The bottom surface of the rigid plate rests against segments 8 and 18 of the spinal column to be fused, and is preferably configured to accommodate the shape of the bone against which it is to be attached. This plate must be of sufficient rigidity to carry the load that would normally be carried by the bone to which the plate is attached. It is preferable that the plate is formed of a biocompatible, corrosion resistant metal such as, for example, stainless steel, cobalt-chromium-molybdenum alloy or a titanium alloy. Of course, these are only exemplary materials and the plate may be formed of any biocompatible material that is sufficiently strong and rigid.

Typically plates to be used with the present invention have a height dimension (i.e. plate thickness) in a direction normal to the surface of the bone to which the plate is to be attached. This thickness is the shortest distance between the top surface and bottom surface. The length of the plate is that dimension that is parallel to the longitudinal axis of the bone to which the plate is to be attached. The width of the plate is typically that dimension that is normal to the length dimension.

Compression plates used for healing bones possess multiple openings to accommodate the insertion of screws (for example 9 and 10 on FIG. 3), therethrough. These openings are placed along the length of the plate so that when the plate is situated along a bone expressing disc, 13, to be fused, there are openings on both sides of the fracture so that the attaching implements can be secured to the spinal segments on opposite sides of the disc. The openings extend from the top (outer) surface of the plate through to the bottom (inner) surface of the plate. In addition, the plate has a plurality of elongate openings extending in a direction parallel to the longitudinal central axis of the plate that permit adjustability in locating the plate along the spinal column or long bone.

In operation, vertebrae, or spinal segments V (FIG. 3) between which a bone graft G has been positioned, are held in a suitable position for fusion and healing by screws 10. Screws 10 are secured into the spinal segments either side of the graft using first nuts 15. Plate 14 is inserted over the secured screws that are protruding out of the bone and is held in place with nuts 12 of the present invention. The load transmitted through the plate assembly may be determined by the initial torque applied to the nut, and by the nature of the polymer insert of the nut. Polymer insert preferably has a substantially uniform thickness profile. However it is envisioned that this thickness may be varied depending on the application and the amount of movement required by the bone plate or the attaching implement.

When the bone plate assembly is attached to the spinal segments to be fused, the bone is in a compressed state with the plate assembly under tension due to compression of the bone by the screws and the plate. This tension may be achieved by drilling holes in the bone that are slightly further apart than the openings in the plate. Thereafter, when the screws and/or nuts are tightened and the plate is placed under tension, the bone will be forced into a compressed state amenable for healing.

In operation, the thickness profile of the polymer insert will generally change through wear and continued compression. This change will allow the screws with which the plate is attached to the bone a greater degree of movement which facilitates, over a period of time, a gradual decrease in the load carried by the bone plate assembly and a concomitant increase in the load carried by the healing bone. The polymer member is formed preferably either from a viscoclastic material or a resorbable material. Where the polymer is a viscoelastic material it is preferably ultra high molecular weight polyethylene (UHMWPE).

The polyethylene, polypropylenes and their copolymers are called polyolefins. These are thermoplastics (Park and Lakes, 1992). Polyethylene is available commercially in three major grades which are: low density, high density and ultrahigh molecular weight grade. Polyethylene is readily crystallized. The first polyethylene synthesized was by reacting ethylene gas at high pressure (100–300 MPa) in the presence of a catalyst to initiate polymerization to yield low density polyethylene. If a Ziegler catalyst is used high density polyethylene can be generated at pressures of 10 MPa. Ultra high molecule weight polyethylenes have a molecular weight of about $2 \times 10^6$ g/mol or greater, and these have been extensively used in orthopedic implants especially for load bearing surfaces such as hip and knee joints. The synthesis of polyethylenes and their uses in orthopedics are well know to those of skill in the art. Other suitable viscoelastic materials include but are not limited to polyethylene, ultra high molecular weight polyethylene polypropylene, polytetrafluoroethylene, polycarbonate, nylon, styrene butadiene rubber, VITON® copolymers, butyl rubber, or nitrile rubber.

Where the material used for forming the polymeric insert is of a resorbable material the polymer member is preferably formed from polyglycolic acid or polylactic acid. Other suitable resorbable material include copolymers of PGA and PLA. Of course these are only exemplary materials to be used for the insert, and those of skill in the art will recognize that other suitable materials may be used in the practice of the invention.

In practice, the polymer material deforms under load and facilitates a change in the thickness profile of the gap between the screw and the polymer insert. This in turn results in a gradual reduction of the pressure of the nut against the bone plate. As this fit becomes looser, the load placed upon the bone is gradually transferred from the bone plate assembly to the bone during the healing process. This transfer of pressure process, which is used herein is referred to as "creep". is advantageous over conventional bone fracture plates which remain rigid throughout the healing process and tend to introduce an undesirable stress shielding effect. This shielding effect may lead to re-fracturing of bone, osteopenia and osteoporosis.

In the cases where the polymer insert is a bioresorbable material, the gradual deformation results in a loss of polymer material from the insert. The present invention provides a unique casing that captures these deposits and greatly reduces the amount of xenobiotic that becomes absorbed by the tissue.

Control of the rate at which creep occurs is important for proper bone healing to take place. The present invention reliably controls the rate of creep, and thus load transfer, as healing takes place. As is shown in FIG. 1A, lip 4 of the nut reduces the amount of polymer escaping. Thus, if creep is to occur it will likely occur by a general loosening of the nut from around the edges of the screw near the top surface of the plate. The creep rates of UHMWPE are measurable, and the rate of creep may therefore be controlled according to the period of time over which the load is transferred from the plate to the bone.

The desired size of the nut and the polymer insert depends on such factors as size and shape of the plate, the number of openings in the plate, the degree of initial compression on the bone, the size of the screws to be used, and the type of bone to be healed and so forth.

The following examples are included to demonstrate preferred embodiments of the invention. It will be appreciated by those of skill in the art that the techniques and apparatus disclosed in the examples that follow represent techniques and apparatus discovered by the inventors to function well in the practice of the invention, and thus can be considered to constitute preferred modes for its practice. However, those of skill in the art will, in light of the present disclosure, appreciate that many changes can be made in the specific embodiments that are disclosed and still obtain a like or similar result without departing from the spirit and scope of the invention.

EXAMPLE I

Production of Representative Nut and Polymer Insert

Stainless steel (type 304) was used to make the nut casing, and UHMWPE was used to make the nut and polymer insert. Representative dimensions of the nut are shown in FIG. 2. The thickness of the polymer insert in this Example was about 1 mm. In other methods, about 2 mm or about 3 mm or about 4 mm are suitable for polymer thickness. In one method of practicing the invention, the sides of the nuts were machined first using a CNC machine (Centurion R. Milltronics Co., Chanhanssen, Minn.), then undercutting the inside hole with an EDM machine (CS-1 EDM machine, Hansvedt Co., Urbana, Ill.). The polymer insert was first machined from a solid block into a cylindrical form, and a hole was then drilled out in the center of the polymer insert after insertion into the nut. The lip of the nut was fashioned to hold the polymer in place. See FIG. 2. The invention was tested with a control nut having no insert. In the present example, one type of commercially available control nut, plate and screw was used (Acromed, Inc., Cleveland, Ohio).

It is recognized that the polymer insert may be held in place by other means. For example, the inside surface of the nut and the outside surface of the polymer insert may be machined with threads such that they may be threaded together. Other means of attachment of the polymer to the nut include, but are not limited to, friction, adhesives or heat bonding.

EXAMPLE II

Testing of Loosening Torque

Figure 5:
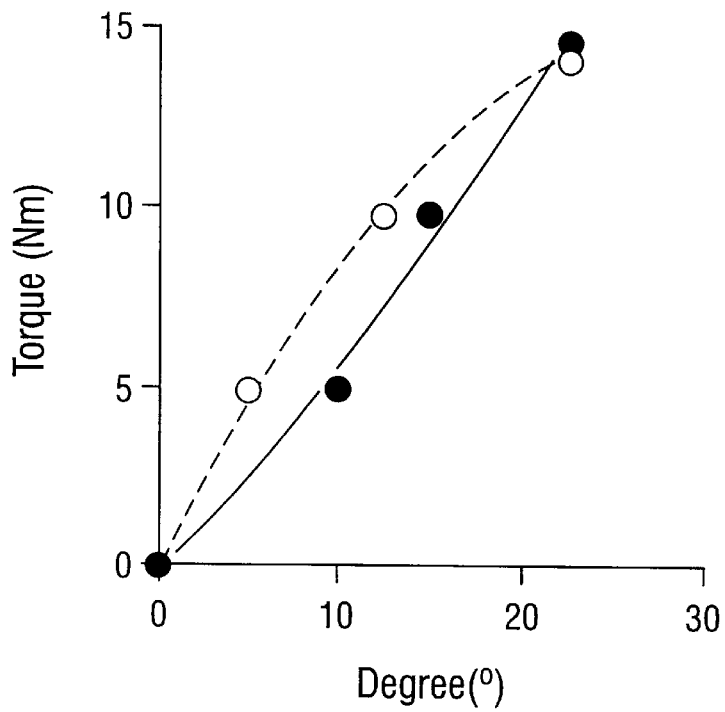
FIG. 5 is a graph showing torque versus degree of rotation during tightening to achieve 5, 10, and 15 Newton meters (Nm).

Pedicle plate (14), screw (15), and nut (16) were assembled as shown in FIG. 5 and secured with a torque wrench. The angle of rotation was measured and the torque determined. The tightening and untightening angles were recorded at 5, 10, and 15 Nm torque. For each torque level, two prior art control (Acromed, Inc., Cleveland, Ohio) and two nuts of the present invention were tested resulting in 6 paired test specimens.

Figure 6:
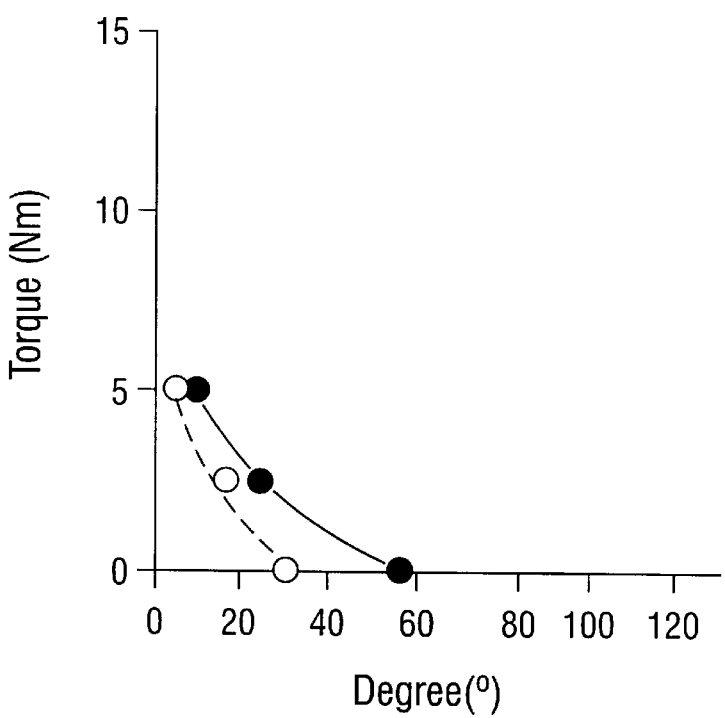
FIG. 6 is a graph showing comparative rotation movements needed to loosen a conventional nut (dotted line) and a polymer containing nut (solid line) from a 5 Nm torque level.
Figure 7:
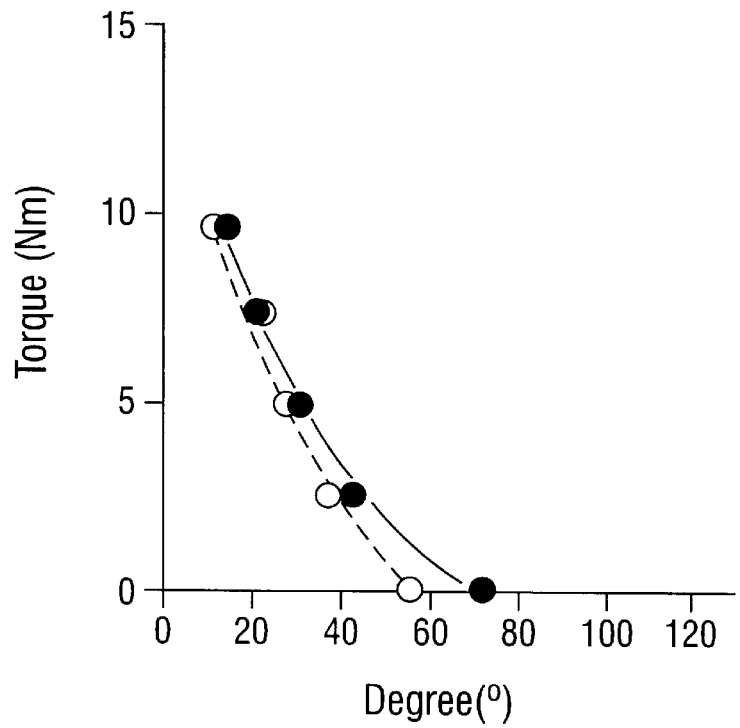
FIG. 7 is a graph showing torque versus degree of (counter) rotation during loosening from 10 Nm of torque for control (dotted line) and polymer containing (solid line) specimens.
Figure 8:
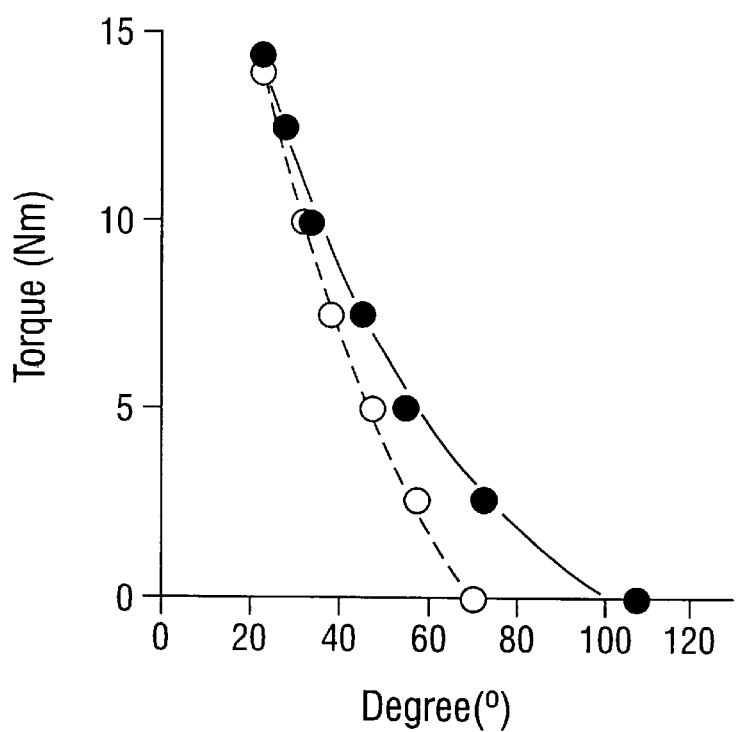
FIG. 8 is a graph showing torque versus degree of (counter) rotation during loosening from 15 Nm of torque for control (dotted line) and polymer containing (solid line) specimens.
Figure 9:
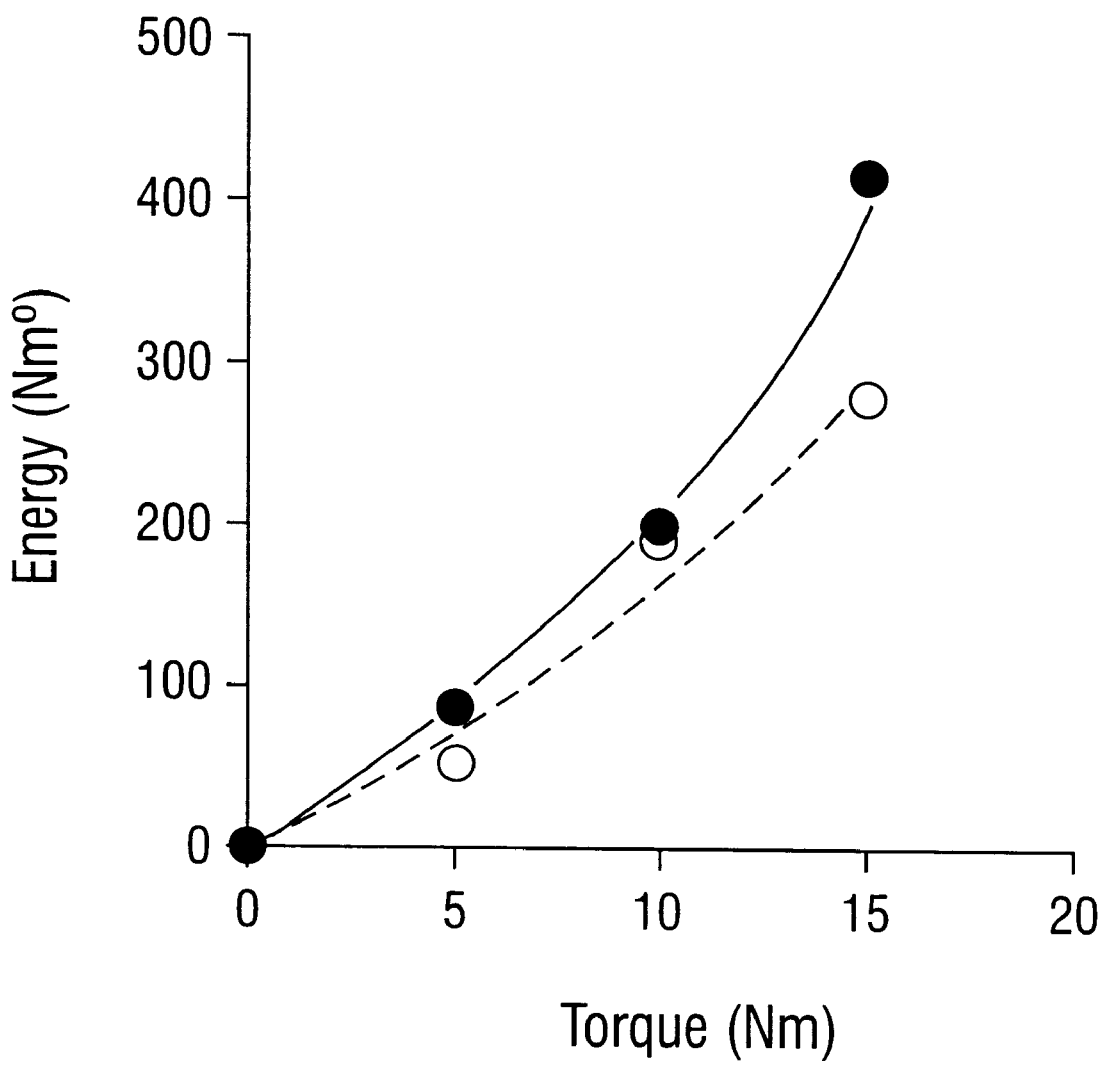
FIG. 9 is a graph showing energy to loosen the nut versus initial tightening torque level for control (dotted line) and polymer containing (solid line) specimens.

The results of the torque tests are shown in Table 1, and the tightening torques versus degrees of rotation are shown in FIG. 5. The control nuts (dashed curve) tended to achieve the desired torque level with smaller rotation than the nuts of the present invention (solid curve), indicating the polymer insert is being deformed and compressed before achieving the same level of torque as the nut without the insert. FIG. 6, FIG. 7 and FIG. 8 show the untightening torque versus degree of rotation for 5, 10, and 15 Nm. The untightening torque study showed that the (counter) rotation of the nuts with polymer inserts is consistently greater than the control nuts at three different levels of the initial torque. As shown in FIG. 9, the results indicate that the energy required to loosen the nuts with the inserts is generally greater than the control nuts. As calculated in the present studies, the energy of rotation is obtained by integrating the torque versus rotation angle curves.

TABLE 1

| Torque | Experi-mental (E1) | Experi-mental (E2) | Experi-mental (average) | Control (C1) | Control (C2) | Control (average) |
| --- | --- | --- | --- | --- | --- | --- |
| 5 Nm | | | | | | |
| 5 | 10 | 10 | 10 | 5 | 5 | 5 |
| 2.5 | 27.5 | 22.5 | 25 | 12.5 | 20 | 16.25 |
| 0 | 52.5 | 60 | 56.25 | 30 | 30 | 30 |
| 10 Nm | | | | | | |
| 10 | 15 | 15 | 15 | 15 | 10 | 12.5 |
| 7.5 | 20 | 22.5 | 21.25 | 22.5 | 22.5 | 22.5 |
| 5 | 30 | 32.5 | 31.25 | 27.5 | 30 | 28.75 |
| 2.5 | 42.5 | 45 | 43.75 | 35 | 40 | 37.5 |
| 0 | 70 | 75 | 72.5 | 50 | 60 | 55 |
| 15 Nm | | | | | | |
| 14 | 20 | 25 | 22.5 | 25 | 20 | 22.5 |
| 10 | 32.5 | 35 | 27.5 | 30 | 25 | 27.5 |
| 7.5 | 45 | 45 | 45 | 40 | 30 | 32.5 |
| 2.5 | 75 | 70 | 72.5 | 70 | 45 | 57.5 |
| 0 | 105 | 110 | 107.5 | 80 | 60 | 70 |

EXAMPLE III

Use of the Spinal Plate and Screw System for Healing

In instances where support is required following spinal surgery, such as disc replacement with a bone graft, or other spinal trauma, it may be desirable to support the affected vertebral bodies in a desired and predetermined relationship to prevent load from being transmitted through the spine during healing. As set forth above, healing is accelerated when such a load is allowed to gradually return to the spine as healing progresses.

The surgically implantable device shown in FIG. 3 includes at least one plate connected with the spinal segments or vertebral bodies V of spinal column C by a plurality of fasteners. Plate is of sufficient length to span at least two, and preferably four, different vertebral bodies V. The plate is bendable to conform to a desired curvature of the portion of spinal column C spanned.

The fasteners includes a screw, first nut, and a nut with polymer insert according to the present invention. Each of the fasteners connects the plate with a respective one of the vertebral bodies V. As seen in FIG. 3, screw 10 has a first threaded portion 17 for threaded engagement with a corresponding opening in the vertebral body V, and a second threaded portion 18 that engages with first nut 15 and second nut 12 having the polymer insert. A hex head end portion of screw 10 is used to thread the screw into the opening in vertebrae V. Screw 10 also has an intermediate portion (not shown) having a configuration, such as a hexagonal configuration, allowing gripping by a suitable tool.

Following insertion of screw into the opening in the vertebrae, first nut 15 may then be applied to screw 10 over second threaded portion 18 to secure screw 10 into the vertebrae V. In certain other embodiments, first nut is not used. Plate 14 is then placed over second threaded portion 18 of screw 10. Nut 12 having the polymer insert is then threaded onto second threaded portion 18 and is tightened against the plate. A suitable tool may be used to grip intermediate portion of screw 10 to prevent rotation of screw 10 during nut installation. Nut 12 is tightened to a sufficient torque to maintain the position of plate 14 relative to screw 10 and vertebrae V. As such, load is transferred between vertebral body V to screw 10 and nut 12 and to plate 14.

As used in the present invention, the polymer insert in nut 12 will plastically deform over time under the load transmitted between the vertebrae V, screw 10, and plate 14. As set forth above, the load transmitted to the plate will decrease over time because the polymer insert deforms and loses compression over time. This results in the load of the spinal column that is carried by plate 14 being transferred from plate 14 through the vertebral bodies V adjacent to plate 14 and to the vertebral bodies V connected to plate 14. In essence, a relatively large percentage of the load of the spinal column that is carried by plate 14 is gradually transferred to the vertebrae in spinal column C covered by plate 14 that require healing.

While the apparatus and methods of this invention have been described in terms of preferred embodiments, it will be apparent to those of skill in the art that variations may be applied to the apparatus, methods and in the steps or in the sequence of steps of the method described herein without departing from the concept, spirit and scope of the invention. More specifically, it will be apparent that certain compositions that are both chemically and physiologically related may be substituted for the polymers described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Christal et al., "In vivo fate of bioresorbable bone plates in long-lasting poly (L-lactic acid" In Second Trans. World Congress on Biomaterials, Apr. 27–May 1, Washington D.C. 279, 1984.

Park J. B. & Lakes R. S. In "Blomaterials: An Introduction" Plenum Press New York, 1992.

What is claimed is:

1. A fastener for connecting a surgically implantable device for connecting together at least one pair of vertebral bodies of the spinal column, the fastener comprising:
    a) a nut casing defining a central passageway and having an outside surface and an inside surface; and
    b) a relaxative polymeric material lining the inside surface.

2. The fastener of claim 1 wherein the polymeric lining is adapted to engage a surgical screw in a firm threaded relationship.

3. The fastener of claim 1, wherein the polymeric lining is sufficiently relaxative to deform as a function of time and stress.

4. The fastener of claim 3 wherein the polymeric lining comprises a ultra high molecular weight polymer.

5. The fastener of claim 3, wherein the relaxative polymeric material comprises polyethylene, polypropylene, polytetrafluoroethylene, polycarbonate, nylon, styrene butadiene rubber, copolymers of vinylidene fluoride and hexafluoropropylene, butyl rubber, or nitrile rubber.

6. The fastener of claim 3, wherein the polymeric lining comprises an ultra high molecular weight polyethylene.

7. The fastener of claim 3 wherein the polymeric lining is bioresorbable.

8. The fastener of claim 7, wherein the polymeric lining comprises polylactic acid, polyglycolic acid, or copolymers thereof.

9. The fastener of claim 1, wherein the casing comprises a biocompatible material that is rigid and durable.

10. The fastener of claim 9, wherein the biocompatible material comprises stainless steel, cobalt-chromium-molybdenum alloy or titanium alloy.

11. A method for surgically implanting a device for connecting together at least one pair of vertebral bodies of the spinal column, the method comprising:
    a) anchoring bone screws into at least two vertebral bodies;
    b) placing a pedicle plate between the vertebral bodies and longitudinally with the spinal column, said plate defining holes configured to receive the surgical screws and compressively force the bone together at the fracture when the plate is urged against the fractured bone; and
    c) engaging the threads of each surgical screw with a relaxatively lined nut to urge the plate against the fractured bone for a time sufficient to allow the spinal column to heal but relaxes the compressive force during the course of such healing.

12. The method of claim 11 which further comprises engaging each surgical screw with its respective nut to a torque level sufficient to provide for the healing time but also to relax the compressive force in time to inhibit osteoporosis.

13. A fastening system for connecting a surgically implantable pedicle plate to a fractured bone, the fastener comprising:
    (a) at least two surgical screws for affixing the pedicle plate across the fracture to fractured parts of the bone and compressing the parts across the fracture; and
    (b) a nut casing for each screw, said nut casing defining a central passageway and having an outside surface and an inside surface and including a relaxative polymeric lining that engages the inside surface of said casing and receives said surgical screw in a threaded relationship.

14. A kit for connecting a surgically implantable pedicle plate to a fractured bone said kit comprising:
    (a) a surgically implantable pedicle plate; and
    (b) a fastener comprising:
    (1) at least two surgical screws for affixing the pedicle plate across the fracture to fractured parts of the bone and compressing the parts across the fracture; and
    (2) a nut casing for each screw, said nut casing defining a central passageway and having an outside surface and an inside surface and including a relaxative polymeric lining that engages the inside surface of said casing and receives said surgical screw in a threaded relationship.

15. The fastening system of claim 13 wherein the nut is adjustable by selective tightening to thereby adjust the load transmitted between the bone and the pedicle plate.

16. The fastening system of claim 13 wherein the nut is tightened to allow creep over time.

17. A kit for connecting together at least one pair of vertebral bodies of the spinal column with a surgically implantable device, the kit comprising:
   a) a pedicle plate configured to be placed between the vertebral bodies and longitudinally with the spinal column, said plate defining holes configured to receive surgical screws;
   b) a plurality of surgical screws adapted at a first end to be anchored in the vertebrae and threaded at a second end to pass through said holes in a structural relationship to apply a compressive force with said vertebrae; and
   c) a nut for each surgical screw, said nut including a nut casing and a polymeric lining within the nut casing, said polymeric lining having a outer surface adapted to engage the nut casing and an inner surface configured to receive the second end of said surgical screw in a threaded engagement, said polymeric lining being capable of sufficient creep to relax the extent of such threaded engagement with time.

18. A kit as defined in claim 17, wherein each said nut casing includes a lip at one end facing away from the surgical screw within the nut casing and configured to restrain polymeric lining within the nut casing from exiting the nut casing.

19. A nut for securing a surgically implantable device comprising:
   a) a nut casing which is biocompatible and has a central passageway and a top surface, and
   b) a relaxative polymeric member insertable within said passageway and capable of engaging a screw member in a threaded relation.

20. A nut of claim 19, wherein the polymeric member plastically deforms as a function of time and stress.

21. A nut of claim 20, wherein the polymeric member that plastically deforms comprises polyethylene, polypropylene, polytetrafluoroethylene, polycarbonate, nylon, styrene butadiene rubber, copolymers of vinylidene fluoride and hexafluoropropylene, butyl rubber, or nitrile rubber.

22. A nut of claim 21, wherein the polymeric member is biosorbable.

23. A nut of claim 20, wherein the top surface of the nut is capped.

24. A nut of claim 20, wherein the polymeric member comprises a threaded inside surface.

25. A nut of claim 20 wherein the polymeric member has a smooth inside surface.

\* \* \* \* \*